United States Patent
Govari et al.

(10) Patent No.: US 7,301,332 B2
(45) Date of Patent: Nov. 27, 2007

(54) MAGNETIC SENSOR ASSEMBLY

(75) Inventors: Assaf Govari, Haifa (IL); Andres Claudio Altmann, Haifa (IL); Yaron Ephrath, Kakur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 11/244,719

(22) Filed: Oct. 6, 2005

(65) Prior Publication Data

US 2007/0080682 A1    Apr. 12, 2007

(51) Int. Cl.
G01B 7/30    (2006.01)

(52) U.S. Cl. .......................... 324/207.21; 324/207.24; 600/424; 600/117

(58) Field of Classification Search .............................
324/207.2–207.25, 247–252; 600/424, 117,
600/407; 702/94, 153
See application file for complete search history.

(56) References Cited

U.S. PATENT DOCUMENTS

| | | | |
|---|---|---|---|
| 4,533,872 A | | 8/1985 | Boord et al. |
| 4,849,692 A | | 7/1989 | Blood |
| 4,945,305 A | | 7/1990 | Blood |
| 5,391,199 A | | 2/1995 | Ben-Haim |
| 5,443,489 A | | 8/1995 | Ben-Haim |
| 5,453,686 A | | 9/1995 | Anderson |
| 5,583,436 A | * | 12/1996 | Van De Walle et al. .... 324/252 |
| 5,644,230 A | | 7/1997 | Pant et al. |
| 5,689,185 A | * | 11/1997 | Widdershoven et al. .... 324/252 |
| 6,184,680 B1 | | 2/2001 | Shinoura et al. |
| 6,239,724 B1 | | 5/2001 | Doron et al. |
| 6,278,271 B1 | | 8/2001 | Schott |
| 6,304,082 B1 | * | 10/2001 | Gualtieri et al. ............ 324/252 |
| 6,332,089 B1 | | 12/2001 | Acker et al. |
| 6,522,132 B1 | | 2/2003 | Vieux-Rochaz et al. |
| 6,536,123 B2 | | 3/2003 | Tamura |
| 6,618,612 B1 | | 9/2003 | Acker et al. |
| 6,690,963 B2 | | 2/2004 | Ben-Haim et al. |
| 2002/0065455 A1 | | 5/2002 | Ben-Haim et al. |
| 2003/0120150 A1 | | 6/2003 | Govari |
| 2003/0231098 A1 | | 12/2003 | Wan |
| 2004/0068178 A1 | | 4/2004 | Govari |
| 2004/0147920 A1 | | 7/2004 | Keidar |
| 2005/0242805 A1 | * | 11/2005 | Honkura et al. ............ 324/249 |

FOREIGN PATENT DOCUMENTS

| | | |
|---|---|---|
| EP | 1530057 A2 | 5/2005 |
| WO | WO 96/05768 A1 | 2/1996 |
| WO | WO 01/04656 A1 | 1/2001 |

* cited by examiner

*Primary Examiner*—Jay M Patidar
(74) *Attorney, Agent, or Firm*—Louis J. Capezzuto

(57) ABSTRACT

A sensor assembly includes a first magneto-resistive field sensor in a first surface-mountable package, which measures first and second components of a magnetic field projected onto respective different first and second axes with respect to a spatial orientation of the sensor and to produce first position signals indicative of the measured first and second components. A second magneto-resistive field sensor in a second surface-mountable package measures at least a third component of the magnetic field projected onto at least a third axis with respect to the spatial orientation of the sensor, and to produce second position signals indicative of the measured third component. A substrate assembly orients the first field sensor in a first spatial orientation and to orient the second field sensor in a second spatial orientation so that the third axis is oriented out of a plane containing the first and second axes.

13 Claims, 2 Drawing Sheets

MAGNETIC SENSOR ASSEMBLY

FIELD OF THE INVENTION

The present invention relates generally to medical position tracking systems, and particularly to methods and devices for sensing a magnetic field in a magnetic position tracking system.

BACKGROUND OF THE INVENTION

Various methods and systems are known in the art for tracking the coordinates of objects involved in medical procedures. Some of these systems use magnetic field measurements. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe, such as a catheter. A position sensor is placed in the probe and generates signals in response to externally-applied magnetic fields. The magnetic fields are generated by magnetic field generators, such as radiator coils, fixed to an external reference frame in known, mutually-spaced locations.

Additional methods and systems that relate to magnetic position tracking are described, for example, in PCT Patent Publication WO 96/05768, U.S. Pat. Nos. 4,849,692, 4,945,305, 5,453,686, 6,239,724, 6,332,089, 6,618,612 and 6,690,963 and U.S. Patent Application Publications 2002/0065455 A1, 2003/0120150 A1, 2004/0068178 A1 and 2004/0147920 A1, whose disclosures are all incorporated herein by reference. These publications describe methods and systems that track the position of intrabody objects such as cardiac catheters, orthopedic implants and medical tools used in different medical procedures.

Some position tracking systems, including some of the systems described in the above-mentioned references, use alternating-current (AC) magnetic fields. Other position tracking systems, such as the systems described in U.S. Pat. Nos. 4,849,692, 4,945,305 and 5,453,686 cited above use direct-current (DC) fields.

Several position sensors and sensor assemblies for sensing magnetic fields are known in the art. For example, U.S. Pat. No. 6,536,123, whose disclosure is incorporated herein by reference, describes a hybrid three-axis magnetic sensor for calculating the direction of the earth magnetism. The sensor includes a flux gate type magnetic sensor which is so formed that a base serves as a main member and detects two axis components of a magnetic vector defined by a plane parallel to the base. A Hall element detects another component of the magnetic vector orthogonal to the base. A tilt sensor detects a tilt angle of the base. The flux gate type magnetic sensor and the Hall element are integrally structured together as a hybrid IC. The detected three-dimensional magnetic vector is corrected in light of the inclination of the base.

As another example, U.S. Pat. No. 6,278,271, whose disclosure is incorporated herein by reference, describes a magnetic field sensor for measurement of the three components of a magnetic field. The sensor comprises a Hall-effect element and an electronic circuit. The Hall-effect element comprises an active area, which is contacted with voltage and current contacts. Four voltage contacts are connected to inputs of the electronic circuit. By means of summation or differential formation of the electrical potentials present at the voltage contacts, the electronic circuit derives three signals proportional to the three components of the magnetic field.

U.S. Pat. No. 6,184,680, whose disclosure is incorporated herein by reference, describes a magnetic field sensor in which a magnetic film or films having a magneto-resistance effect for detecting a magnetic field and a conductor electrode film for applying a current to the magnetic film are deposited on a flexible substrate.

Magnetic field sensors sometimes comprise magneto-resistive sensors. For example, several magnetic field sensors and modules based on magneto-resistive elements are produced by Honeywell International Inc. (Morristown, N.J.).

Information regarding these products can be found at www.ssec.honeywell.com/magnetic/products.html. Philips Electronics (Amsterdam, The Netherlands) also produces magneto-resistive field sensors. Details regarding these products can be found at www.semiconductors.philips.com.

SUMMARY OF THE INVENTION

In many medical position tracking applications, it is desirable that the position sensor fitted in the probe measure all three orthogonal components of the externally-applied magnetic field. However, many conventional magnetic field sensors can only measure one or two of these components. In particular, it is difficult to manufacture triple-axis magnetic field sensors using surface-mount technology (SMT). On the other hand, single-axis and dual-axis SMT field sensors are often attractive candidates for use in sensor assemblies, because of their low cost, small size and profile, and their suitability for conventional high-volume manufacturing processes.

Embodiments of the present invention thus provide magnetic sensor assemblies, position sensors and methods for producing such assemblies and sensors, that combine two or more single- or dual-axis field sensors to measure all three magnetic field components.

In some embodiments, the field sensors comprise magneto-resistive elements able to measure DC magnetic fields. Advantageously, DC sensors are less susceptible to measurement errors caused by disturbances from metallic objects than are AC field sensors.

In some embodiments, the field sensors are mounted on a substrate assembly, which orients the sensors in different, respective geometrical planes, so as to enable them to jointly measure the magnetic field and produce position signals indicative of all three components of the field. In some embodiments, the substrate assembly comprises a flexible PCB, which is bent into a suitable three-dimensional shape. In alternative embodiments, the substrate assembly comprises two or more slotted substrate sections that are interlocked with one another, so as to position the field sensors on different geometrical planes.

Typically, the substrate assembly comprises conventional printed circuit board (PCB) material, and the sensor assembly can be produced using conventional PCB fabrication and assembly processes.

There is therefore provided, in accordance with an embodiment of the present invention, a sensor assembly, including:

a first magneto-resistive field sensor in a first surface-mountable package, which is arranged to measure first and second components of a magnetic field projected onto respective different first and second axes with respect to a spatial orientation of the first field sensor and to produce first position signals indicative of the measured first and second components;

a second magneto-resistive field sensor in a second surface-mountable package, which is arranged to measure at least a third component of the magnetic field projected onto at least a third axis with respect to the spatial orientation of the second field sensor, and to produce second position signals indicative of the measured third component; and a substrate assembly having the first and second field sensors surface-mounted thereon, which is coupled to orient the first field sensor in a first spatial orientation and to orient the second field sensor in a second spatial orientation so that the third axis is oriented out of a plane containing the first and second axes.

In an embodiment, the substrate assembly includes a flexible substrate material bent so as to orient the first and second field sensors. The flexible substrate material may include one or more slots so as to enable bending the substrate assembly.

In another embodiment, the substrate assembly includes two or more sections interlocked into one another so as to orient the first and second field sensors. The two or more sections may include at least one slot so as to enable interlocking the sections into one another.

In yet another embodiment, the substrate assembly includes a printed circuit board (PCB) material. In some embodiments, electrical conductors are disposed on the PCB material so as to provide electrical interconnection for at least one of the first and second field sensors.

In still another embodiment, the sensor assembly has a size smaller than 2 by 2 by 4 mm.

There is also provided, in accordance with an embodiment of the present invention, a position sensing apparatus, including:

one or more field generators, which are arranged to generate a magnetic field;

a sensor assembly, including:

a first magneto-resistive field sensor in a first surface-mountable package, which is arranged to measure first and second components of the magnetic field projected onto respective different first and second axes with respect to a spatial orientation of the first field sensor and to produce first position signals indicative of the measured first and second components;

a second magneto-resistive field sensor in a second surface-mountable package, which is arranged to measure at least a third component of the magnetic field projected onto at least a third axis with respect to the spatial orientation of the second field sensor, and to produce second position signals indicative of the measured third component; and a substrate assembly having the first and second field sensors surface-mounted thereon, which is coupled to orient the first field sensor in a first spatial orientation and to orient the second field sensor in a second spatial orientation, so that the third axis is oriented out of a plane containing the first and second axes; and a control module, which is arranged to receive the first and second position signals and to calculate a spatial position of the sensor assembly with respect to the one or more field generators responsively to the position signals.

In an embodiment, the magnetic field includes a direct current (DC) magnetic field.

In another embodiment, the position sensor is adapted to be coupled to an object inserted into a body of a patient, and the control module is arranged to determine position coordinates of the object inside the body.

There is additionally provided, in accordance with an embodiment of the present invention, a method for producing a sensor assembly, including:

providing a first magneto-resistive field sensor in a first surface-mountable package, which is arranged to measure first and second components of a magnetic field projected onto respective different first and second axes with respect to a spatial orientation of the first field sensor and to produce first position signals indicative of the measured first and second components;

providing a second magneto-resistive field sensor in a second surface-mountable package, which is arranged to measure at least a third component of the magnetic field projected onto at least a third axis with respect to the spatial orientation of the second field sensor, and to produce second position signals indicative of the measured third component;

surface-mounting the first and second field sensors on a substrate assembly so as to orient the first field sensor in a first spatial orientation and to orient the second field sensor in a second spatial orientation, so that the third axis is oriented out of a plane containing the first and second axes.

The present invention will be more fully understood from the following detailed description of the embodiments thereof, taken together with the drawings in which:

DETAILED DESCRIPTION OF EMBODIMENTS

System Description

Figure 1:
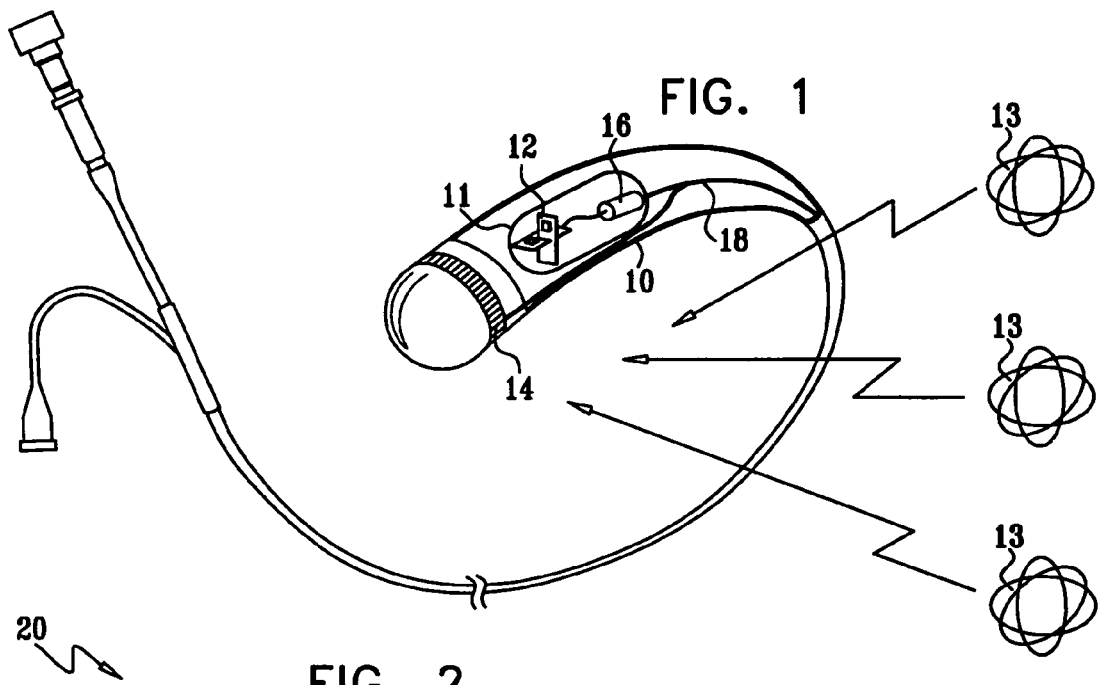
FIG. 1 is a schematic, pictorial illustration of a probe in a magnetic position-tracking system, in accordance with an embodiment of the present invention.

FIG. 1 is a schematic, pictorial illustration of a probe 10 used in a medical 2 5 magnetic position tracking system, in accordance with an embodiment of the present invention. In the exemplary embodiment of FIG. 1, probe 10 comprises a cardiac catheter inserted into a patient's heart for performing cardiac electrical mapping, imaging, therapy and/or other invasive procedures. The catheter is part of a magnetic position tracking system, which generally comprises one or more field generators 13 positioned at known spatial coordinates. The field generators generate magnetic fields in a predetermined working volume comprising the probe.

A position sensor 11 is coupled to probe 10 in order to measure the position coordinates of the probe responsively to the magnetic field in its vicinity. In the present example, the position sensor is fitted in the distal end of the catheter. Position sensor 11 comprises a sensor assembly 12 that senses the magnetic field and produces position signals indicative of the sensed field. Sensor assembly 12 typically comprises two or more compact magnetic field sensors, each capable of measuring components of a magnetic field along one or two axes. The sensors are arranged in a spatial configuration that enables them to measure all three orthogonal components of the externally-applied magnetic field. Exemplary sensor assembly configurations are shown and explained in FIGS. 2-5 below.

In addition to position sensor 11, probe 10 may comprise additional components, such as electrodes 14, as well as additional sensors and/or therapeutic elements (not shown). In some embodiments, position sensor 11 comprises a control module 16 that accepts the position signals and/or other signals produced by probe 10 and sends them via a cable 18 to an external processing unit (not shown). The external processing unit calculates and displays the position of the probe with respect to field generators 13. The calculated position may comprise up to six-dimensional coordinate information, including both position and angular orientation of the probe.

The present patent application is mainly concerned with the structure of position sensor 11 and in particular sensor assembly 12. The specific operation of probe 10 and of the magnetic position tracking system is considered to be outside the scope of this patent application. The cardiac applications described above are mentioned purely by the way of example. The methods and devices described herein can be used in a variety of position-tracking systems and applications, such as systems for diagnosis and treatment of the respiratory, digestive and urinary tracts and systems for tracking orthopedic implants and medical tools, as well as in non-medical applications. Depending on the application, position sensor 11 and/or sensor assembly 12 can be coupled to a catheter, an endoscope, a orthopedic implant, a medical or surgical tool, or to any other suitable tracked object. Some exemplary systems that can use the methods and devices described herein are described in the above-cited publications.

Magnetic Sensor Assembly

In many applications, it is desirable for position sensor 11 to measure all three orthogonal components of the externally-applied magnetic field in order to enable position calculation. For this purpose, in some embodiments, sensor assembly 12 comprises two or more low-profile electronic magnetic field sensors. Such magnetic field sensors may be based on magneto-resistive elements, as are known in the art. The use of magneto-resistive elements is desirable in many cases, since they are able to measure DC magnetic fields, which are less susceptible to measurement errors caused by disturbances from metallic objects than AC fields. Some exemplary magnetic field sensors that can be used in sensor assembly 12 are the Honeywell HMC 1002, HMC 1022, HMC 1052 dual-axis sensors. Further details regarding these devices can be found on the Honeywell web-site cited above.

Typically, conventional magnetic field sensors, such as the Honeywell and Philips devices cited above, comprise one or two miniaturized magneto-resistive elements. These elements measure one, or at most two orthogonal components of the magnetic field projected on a plane parallel to the surface of the device. Most of these devices are small, flat, surface-mount devices (SMD). In principle, measuring all three orthogonal field components implies using three magneto-resistive elements, one of which should be oriented in a plane perpendicular to the surface of the device. Such a configuration is typically difficult to implement in a planar configuration of a small surface-mount device.

Therefore, in some embodiments, sensor assembly 12 comprises a three-dimensional substrate assembly, on which the field sensors are mounted. The substrate assembly positions the field sensors with respect to one another in a spatial orientation that enables them to measure all three components of the externally-applied field.

In some embodiments, the substrate assembly comprises a printed circuit board (PCB). In these embodiments, the substrate assembly may comprise conducting traces for routing the position signals produced by the field sensors. Additionally or alternatively, control module 16 and/or any other electronic circuitry of probe 10 can be fabricated on the substrate of sensor assembly 12.

Figure 2:
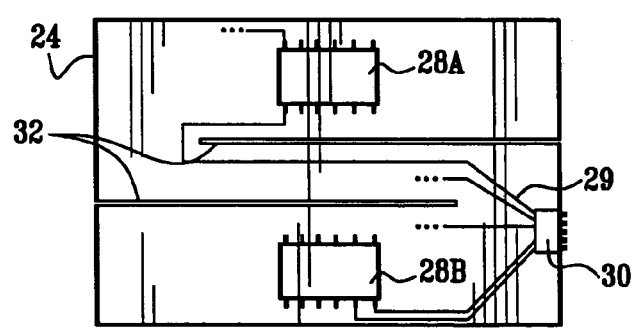
FIG. 2 is a schematic top view showing elements of a sensor assembly, in accordance with an embodiment of the present invention.

FIG. 2 is a schematic top view showing elements of an exemplary sensor assembly 20, which can be used as sensor assembly 12, in accordance with an embodiment of the present invention. In this embodiment, a substrate assembly 24 comprises a flexible substrate, such as a flexible PCB. FIG. 2 shows substrate assembly 24 in its initial flat shape, before it is bent into the proper three-dimensional shape in which it is used in sensor assembly 20. The flexible substrate can be fabricated using any suitable PCB manufacturing process.

Two magnetic field sensors 28A and 28B are mounted on the flexible substrate. Typically, sensors 28A and 28B comprise SMDs mounted on the substrate using a conventional PCB assembly process, such as a reflow process. Only elements essential to the explanation are shown in the figure, with elements such as optional additional circuitry omitted for simplicity. In some embodiments, PCB conductors 29 provide supply voltages and/or route signals from sensors 28A and 28B to an output port 30 of the sensor assembly. Slots 32 are cut through the flexible PCB in order to allow it to be bent into the desired three-dimensional shape.

Figure 3:
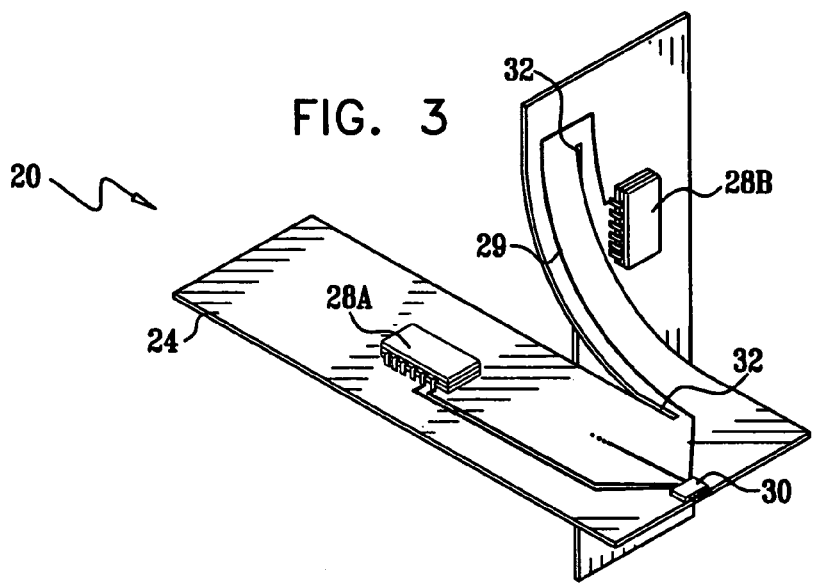
FIG. 3 is a schematic, pictorial illustration of the sensor assembly of FIG. 2, in accordance with an embodiment of the present invention.

FIG. 3 is a schematic, pictorial illustration of sensor assembly 20, in accordance with an embodiment of the present invention. The figure shows flexible substrate assembly 24 of FIG. 2 above, after it is bent into its final, three-dimensional shape. It can be seen that field sensors 28A and 28B are now positioned on two orthogonal planes. In some embodiments, each of sensors 28A and 28B is a dual-axis sensor measuring two orthogonal components of the magnetic field. Thus, when used together, the two sensors provide four position signals indicative of all three orthogonal field components. One of the four position signals may be considered redundant, as it relates to a field component measured by both sensors. In an alternative embodiment, one of sensors 28A and 28B comprises a dual-axis sensor, and the other sensor comprises a single-axis sensor measuring only the third orthogonal field component.

In an alternative embodiment (not shown in the figures), the configuration of flexible substrate assembly 24 can be generalized in a straightforward manner to orient three single-axis field sensors in a mutually-orthogonal configuration.

In a further alternative embodiment, flexible substrate assembly 24 positions sensors 28A and 28B in different, but non-orthogonal planes. Because the planes are not orthogonal, some or all of the position signals may contain projections of more than one magnetic field component. Since the mutual angular orientation of the field sensors is constant and known a-priori, a suitable calculation can extract the three orthogonal field components from the position signals. Such a calculation can be carried out either by control module 16 or by the external processing unit.

The particular shape of substrate assembly 24 in FIGS. 2 and 3 is shown purely as a clarifying example. In alternative embodiments, the flexible substrate can be fabricated and bent into any other suitable shape that orients the magnetic field sensors so as to enable them to measure all three components of the magnetic field. The shape of the flexible substrate can be with or without slots.

After bending assembly 24 into the three-dimensional configuration, the flexible substrate assembly can be held in place to maintain its shape using any suitable method. For example, the entire sensor assembly can be cast in suitable potting or fixed using a suitable mechanical fixture to position sensor 11 or to probe 10.

Using the configuration of FIG. 3, an extremely small-size sensor assembly 20 can be achieved, making it suitable for use in catheters, endoscopes, implants and other medical probes and instruments. A sensor assembly can typically be fitted into a 2 by 2 by 4 mm cube or into a cylinder approximately 4 mm high and 2 mm in diameter.

Figure 4:
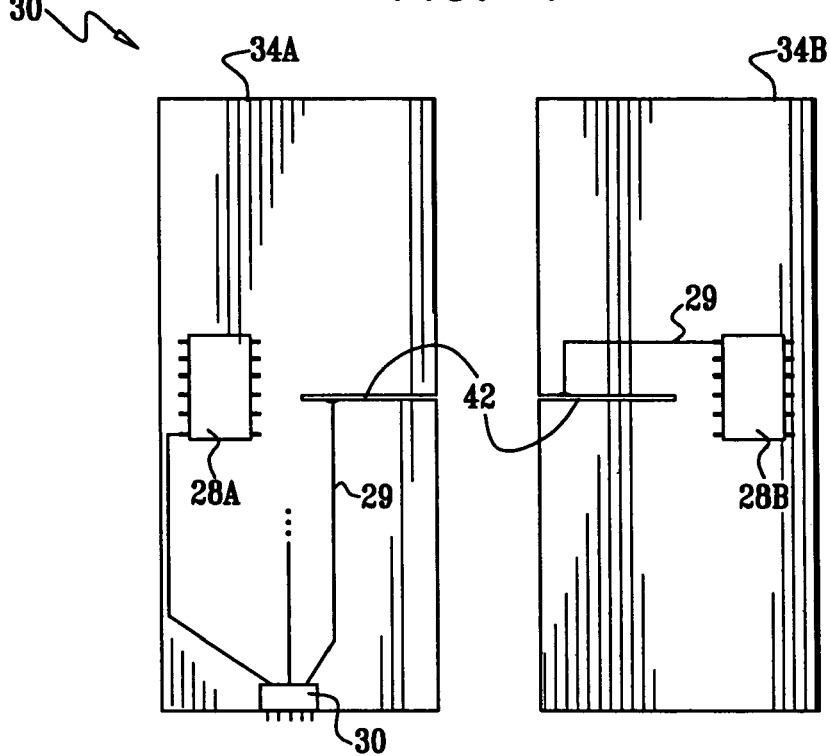
FIG. 4 is a schematic top view showing elements of a sensor assembly, in accordance with another embodiment of the present invention.

FIG. 4 is a schematic top view showing elements of a sensor assembly 30, which can be used as sensor assembly 12, in accordance with another embodiment of the present invention. In this embodiment, the substrate assembly comprises two substrate sections 34A and 34B, typically comprising a suitable rigid PCB material. One of field sensors 28A and 28B is mounted on each substrate section. A slot 42 is cut into one side of each section. Sections 34A and 34B can be manufactured and assembled using any suitable PCB fabrication and assembly methods.

Figure 5:
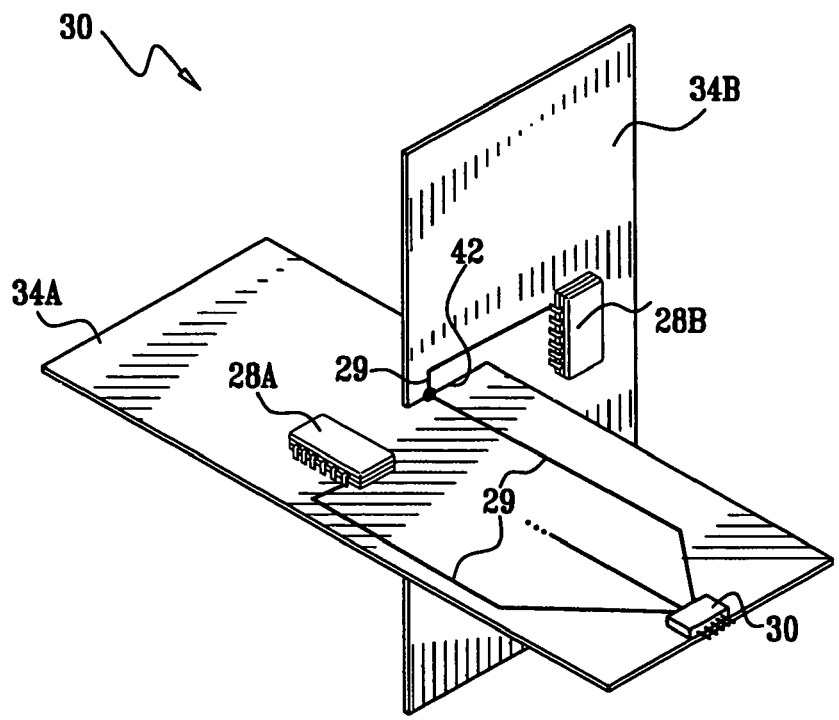
FIG. 5 is a schematic, pictorial illustration of the sensor assembly of FIG. 4, in accordance with an embodiment of the present invention.

FIG. 5 is a schematic, pictorial illustration of sensor assembly 30 of FIG. 4 above, in accordance with an embodiment of the present invention. To form the three-dimensional substrate assembly, sections 34A and 34B are inserted into one another in an orthogonal configuration, using slots 42. Similarly to the configuration of FIG. 3 above, in sensor assembly 30, field sensors 28A and 28B are positioned on two orthogonal planes. When sensors 28A and 28B are dual-axis sensors, the two sensors jointly provide four position signals indicative of the three orthogonal field components, with one component being redundant. Alternatively, one of sensors 28A and 28B may comprise a single-axis sensor.

In some embodiments, PCB conductors 29 connect sensors 28A and 28B with output port 30. Signals may be routed between sections 34A and 34B by having conductors 29 reach slots 42, as shown in FIG. 4. After interlocking sections 34A and 34B, as shown in FIG. 5, the conductors can be soldered or wire-bonded together at slots 42 to provide electrical conductivity.

Alternatively, sections 34A and 34B can be fabricated and attached to one another in any other suitable configuration that enables the field sensors to produce signals indicative of the three magnetic field components. In particular, non-orthogonal configurations may also be used in conjunction with a suitable calculation process. Sensor assembly 30 can be mounted in position sensor 11 or in probe 10 using any suitable mounting method.

Although the methods and devices described hereinabove mainly address sensor assemblies based on magneto-resistive devices, the principles of the present invention can also be used to produce sensor assemblies based on other sensor technologies for sensing DC and/or AC magnetic fields. For example, alternative field sensors may comprise Hall-effect devices or field sensing coils. The sensors may comprise packaged or unpackaged low-profile elements. Additionally, the principles of the present invention can also be used to produce sensor assemblies for sensing other types of fields, such as electric fields as well as for measuring acceleration or other directional properties.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A medical magnetic position tracking system, comprising:
    a probe for insertion into a patient;
    a first magneto-resistive field sensor in a first surface-mountable package, which is arranged to measure first and second components of a magnetic field projected onto respective different first and second axes with respect to a spatial orientation of the first field sensor and to produce first position signals indicative of the measured first and second components;
    a second magneto-resistive field sensor in a second surface-mountable package, which is arranged to measure at least a third component of the magnetic field projected onto at least a third axis with respect to the spatial orientation of the second field sensor, and to produce second position signals indicative of the measured third component; and
    a substrate assembly having the first and second field sensors surface-mounted thereon, which is coupled to orient the first field sensor in a first spatial orientation and to orient the second field sensor in a second spatial orientation so that the third axis is oriented out of a plane containing the first and second axes; and
    a processing unit for receiving the first position signals and the second position signals and calculating six-dimensional coordinate information of the probe.

2. The medical magnetic position tracking system according to claim 1, wherein the substrate assembly comprises a flexible substrate material bent so as to orient the first and second field sensors.

3. The medical magnetic position tracking system according to claim 2, wherein the flexible substrate material comprises one or more slots so as to enable bending the substrate assembly.

4. The medical magnetic position tracking system according to claim 1, wherein the substrate assembly comprises two or more sections interlocked into one another so as to orient the first and second field sensors.

5. The medical magnetic position tracking system according to claim 4, wherein the two or more sections comprise at least one slot so as to enable interlocking the sections into one another.

6. The medical magnetic position tracking system according to claim 1, wherein the substrate assembly comprises a printed circuit board (PCB) material.

7. The medical magnetic position tracking system according to claim 6, and comprising electrical conductors disposed on the PCB material so as to provide electrical interconnection for at least one of the first and second field sensors.

8. The medical magnetic position tracking system according to claim 1, wherein the sensor assembly has a size smaller than 2 by 2 by 4 mm.

9. Medical position sensing apparatus, comprising:
    one or more field generators, which are arranged to generate a magnetic field;

a probe for insertion into a patient, the probe comprising sensor assembly, comprising:

a first magneto-resistive field sensor in a first surface-mountable package, which is arranged to measure first and second components of the magnetic field projected onto respective different first and second axes with respect to a spatial orientation of the first field sensor and to produce first position signals indicative of the measured first and second components;

a second magneto-resistive field sensor in a second surface-mountable package, which is arranged to measure at least a third component of the magnetic field projected onto at least a third axis with respect to the spatial orientation of the second field sensor, and to produce second position signals indicative of the measured third component; and a substrate assembly having the first and second field sensors surface-mounted thereon, which is coupled to orient the first field sensor in a first spatial orientation and to orient the second field sensor in a second spatial orientation, so that the third axis is oriented out of a plane containing the first and second axes; and a control module, which is arranged to receive and send the first and second position signals and a processing unit for receiving the first and second position signals and to calculate a spatial position of the sensor assembly with respect to the one or more field generators responsively to the position signals by calculating up to six-dimensional coordinate information of the probe.

10. The apparatus according to claim 9, wherein the magnetic field comprises a direct current (DC) magnetic field.

11. The apparatus according to claim 9, wherein the substrate assembly comprises a flexible substrate material bent so as to orient the first and second field sensors.

12. The apparatus according to claim 9, wherein the substrate assembly comprises two or more sections interlocked into one another so as to orient the first and second field sensors.

13. The apparatus according to claim 9, wherein the substrate assembly comprises a printed circuit board (PCB) material.

* * * * *